(12) United States Patent
Feurer et al.

(10) Patent No.: US 7,427,617 B2
(45) Date of Patent: Sep. 23, 2008

(54) MORPOLINE-BRIDGED INDAZOLE DERIVATIVES

(75) Inventors: Achim Feurer, Wilhelmsfeld (DE); Joachim Luithle, Wüfrath (DE); Stephan-Nicholas Wirtz, Wuppertal (DE); Gerhard König, Arlington, MA (US); Johannes-Peter Stasch, Solingen (DE); Frank Wunder, Wuppertal (DE); Dieter Lang, Velbert (DE); Elke Stahl, Bergisch Gladbach (DE); Thomas Schenke, Bergisch Gladbach (DE); Rudy Schreiber, Menlo Park, CA (US)

(73) Assignee: Bayer Healthcare AG, Leverkusen (DE)

( * ) Notice: Subject to any disclaimer, the term of this patent is extended or adjusted under 35 U.S.C. 154(b) by 338 days.

(21) Appl. No.: 10/528,601

(22) PCT Filed: Sep. 16, 2003

(86) PCT No.: PCT/EP03/10273

§ 371 (c)(1),
(2), (4) Date: Oct. 14, 2005

(87) PCT Pub. No.: WO2004/031186

PCT Pub. Date: Apr. 15, 2004

(65) Prior Publication Data

US 2006/0128700 A1    Jun. 15, 2006

(30) Foreign Application Priority Data

Sep. 26, 2002    (DE) ................. 102 44 810

(51) Int. Cl.
*C07D 413/14*    (2006.01)
*A61K 31/5386*    (2006.01)

(52) U.S. Cl. .................... 514/230.5; 544/105
(58) Field of Classification Search ................. 544/105; 514/230.5
See application file for complete search history.

(56) References Cited

FOREIGN PATENT DOCUMENTS

| | | |
|---|---|---|
| DE | 19834047 | 2/2000 |
| WO | 9816507 | 4/1998 |
| WO | 9823619 | 6/1998 |
| WO | 0006567 | 2/2000 |
| WO | 0006569 | 2/2000 |
| WO | 0021954 | 4/2000 |
| WO | 0242299 | 5/2002 |
| WO | 0242300 | 5/2002 |
| WO | 0242301 | 5/2002 |
| WO | 0242302 | 5/2002 |

*Primary Examiner*—Kahsay T Habte
(74) *Attorney, Agent, or Firm*—Edwards Angell Palmer & Dodge LLP; Barry Kramer; Ralph Loren

(57) ABSTRACT

The present invention relates to novel morpholine-bridged indazole derivatives having the formula

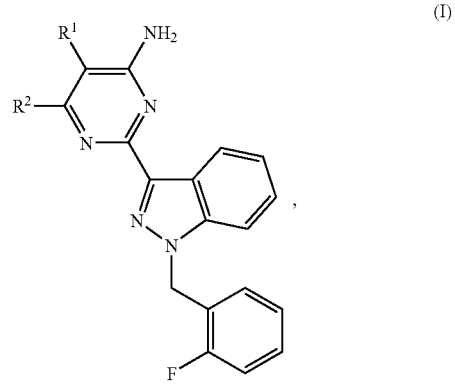

(I)

which stimulate soluble guanylate cyclase, to a process for the preparation thereof, and to pharmaceutical compositions containing them. These compounds are useful for the treatment of disorders of the central nervous system.

5 Claims, No Drawings

MORPHOLINE-BRIDGED INDAZOLE DERIVATIVES

This application is a 371 of PCT/EP2003/010273, filed Sep. 16, 2003.

The present invention relates to novel morpholine-bridged indazole derivatives which stimulate soluble guanylate cyclase, to processes for the preparation thereof, and to the use thereof for producing medicaments, in particular medicaments for the treatment of disorders of the central nervous system.

One of the most important cellular signal transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triposphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and contain at least one heme per heterodimer. The heme groups are part of the regulatory site and are of central importance for the mechanism of activation. NO is able to bind to the iron atom of heme and thus markedly increase the activity of the enzyme. Heme-free preparations cannot, by contrast, be stimulated by NO. CO is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed. In Alzheimers patients for example the NO-stimulated activity of soluble guanylate cyclase in the brain (cerebral cortex) is greatly reduced.

A reduced learning behavior can be observed in experimental animals on administration of dizocilpine, which leads to a reduced cGMP level (Yamada et al., Neuroscience 74 (1996), 365-374). This impairment can be abolished by injecting 8-Br-cGMP, a membrane-permeable form of cGMP. This is consistent with investigations showing that the cGMP level in the brain is increased after learning and memory tasks.

A possible treatment which is independent of NO and aims at influencing the cGMP signal pathway in organisms is a promising approach for stimulating soluble guanylate cyclase because of the high efficiency and few side effects which are to be expected.

Compounds, such as organic nitrates, whose effect is based on release of NO have to date been exclusively used for the therapeutic stimulation of soluble guanylate cyclase. NO is produced by bioconversion and activates soluble guanylate cyclase by binding to the central iron atom of heme. Besides the side effects, the development of tolerance is one of the crucial disadvantages of this mode of treatment.

Substances which directly stimulate soluble guanylate cyclase, i.e. without previous release of NO, have been described in recent years, such as, for example, 3-(5'-hydroxymethyl-2'-furyl)-1-benzylindazole (YC-1, Wu et al., Blood 84 (1994), 4226; Mülsch et al., Br. J. Pharmacol. 120 (1997), 681), fatty acids (Goldberg et al, J. Biol. Chem. 252 (1977), 1279), diphenyliodonium hexafluorophosphate (Pettibone et al., Eur. J. Pharmacol. 116 (1985), 307), isoliquiritigenin (Yu et al., Brit. J. Pharmacol. 114 (1995), 1587) and various substituted pyrazole derivatives (WO 98/16223).

In addition, WO 98/16507, WO 98/23619, WO 00/06567, WO 00/06568, WO 00/06569, WO 00/21954, WO 02/4229, WO 02/4300, WO 02/4301 and WO 02/4302 describe pyrazolopyridine derivatives as stimulators of soluble guanylate cyclase. Also described in these patent applications are pyrazolopyridines having various radicals. Compounds of this type have very high in vitro activity in relation to stimulating soluble guanylate cyclase. However, it has emerged that these compounds have some disadvantages in respect of their in vivo properties such as, for example, their behavior in the liver, their pharmacokinetic behavior, their dose-response relation or their metabolic pathway.

It was therefore the object of the present invention to provide further pyrimidine derivatives which act as stimulators of soluble guanylate cyclase but do not have the disadvantages, detailed above, of the compounds from the prior art. An additional advantage of novel medicaments for the treatment of disorders of the central nervous system (e.g. learning and memory impairments) would be an increased selectivity for peripheral cardiovascular effects. It was likewise intended to improve this (e.g. by better brain penetration) compared with the prior art.

This object is achieved according to the present invention by the compounds of the invention.

Specifically, the present invention relates to compounds of the formula

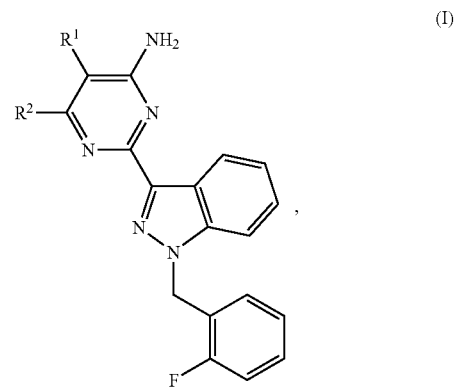

(I)

in which
R¹ is

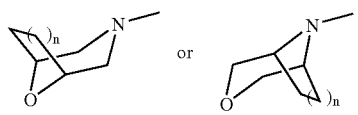

where
n is 1 or 2, and
R² hydrogen or $NH_2$,
and the salts, solvates and/or solvates of the salts thereof.

Where the compounds (I) of the invention contain asymmetric C atoms, they may be in the form of enantiomers, diastereomers or mixtures thereof. These mixtures can be separated in a known manner into the stereoisomenrically pure constituents.

Salts preferred for the purposes of the invention are physiologically acceptable salts of the compounds of the invention.

Physiologically acceptable salts of the compounds according to the invention may be acid addition salts of the compounds with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, citric acid, fumaric acid, maleic acid or benzoic acid.

Physiologically acceptable salts may also be salts with usual bases, such as, for example, alkali metal salts (e.g. sodium or potassium salts), alkaline earth metal salts (e.g. calcium or magnesium salts) or ammonium salts derived from ammonia or organic amines such as, for example, diethylamime, triethylamine, ethyldllsopropylamine, procaine, dibenzylamine, N-methylmorpholine, dihydroabiethylamine, 1-ephenamine or methylpiperidine.

Solvates of the compounds of the invention are for the purposes of the invention stoichiometric compositions of the compounds or of their salts with solvents, e.g. water, ethanol.

For the purposes of the present invention, the substituents generally have the following meaning:

Halogen is fluorine, chlorine, bromine and iodine. Fluorine, chlorine and bromine are preferred, and fluorine and chlorine are particularly preferred.

Preferred compounds of the formula (I) are those in which $R^1$ is

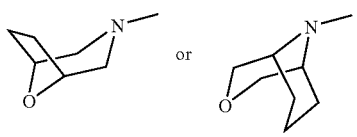

and
$R^2$ is hydrogen or $NH_2$,
and the salts, solvates and solvates of the salts thereof.

Likewise preferred compounds of the formula (I) are those in which
$R^1$ is

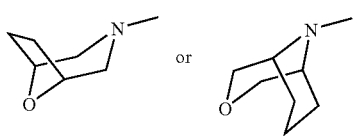

and
$R^2$ is hydrogen,
and the salts, solvates and solvates of the salts thereof.

The compounds of the invention of the formula (I) can be prepared by reacting the compound of the formula

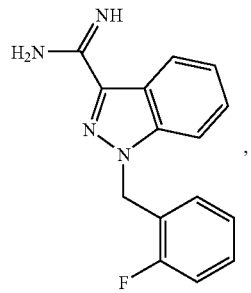

A) with a compound of the formula

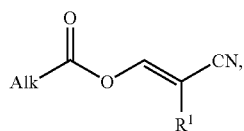

where
$R^1$ has the meanings indicated above and
Alk is $C_1$-$C_4$-alkyl,
or

B) with a compound of the formula

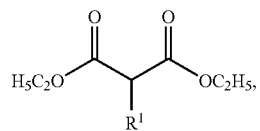

where
$R^1$ has the meanings indicated above,
to give compounds of the formula

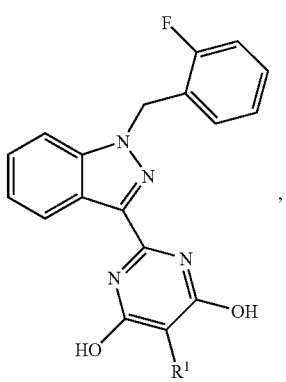

where
$R^1$ has the meanings indicated above,
and subsequently reacting with a halogenating agent to give compounds of the formula

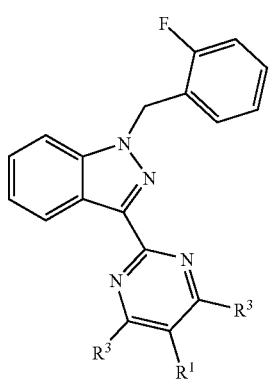

where
R$^1$ has the meanings indicated above, and
R$^3$ is halogen, and final reaction with aqueous ammonia solution with heating under elevated pressure, and by reacting the resulting compounds of the formula (I) where appropriate with the appropriate (i) solvents and/or (ii) bases or acids to give the solvates, salts and/or solvates of the salts thereof.

The compound of the formula (II) can be prepared as shown in the following reaction scheme:

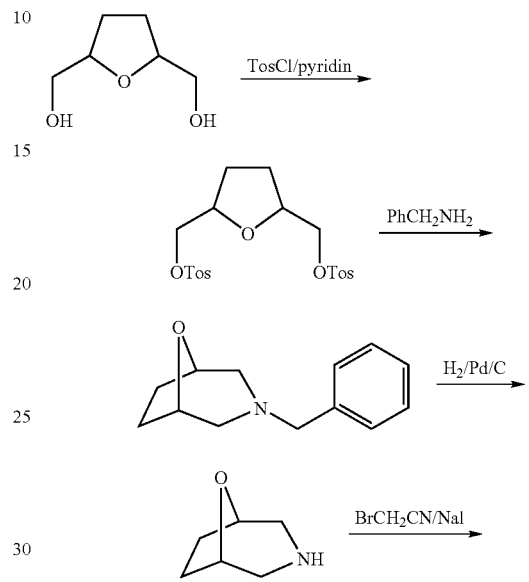

The compound of the formula (II) can be obtained in a two-stage synthesis from 3-cyanoindazole which is known from the literature (Salkowski, H.; Chem.Ber.; 17; 1884; 506 and Chem.Ber.; 22; 1889; 2139) and 2-fluorobenzyl bromide in an inert solvent and in the presence of a base and a subsequent reaction of the nitrile derivative with sodium ethoxide and final reaction with ammonium chloride.

The compounds of the formula (III) can be prepared for example as shown in the following schemes:

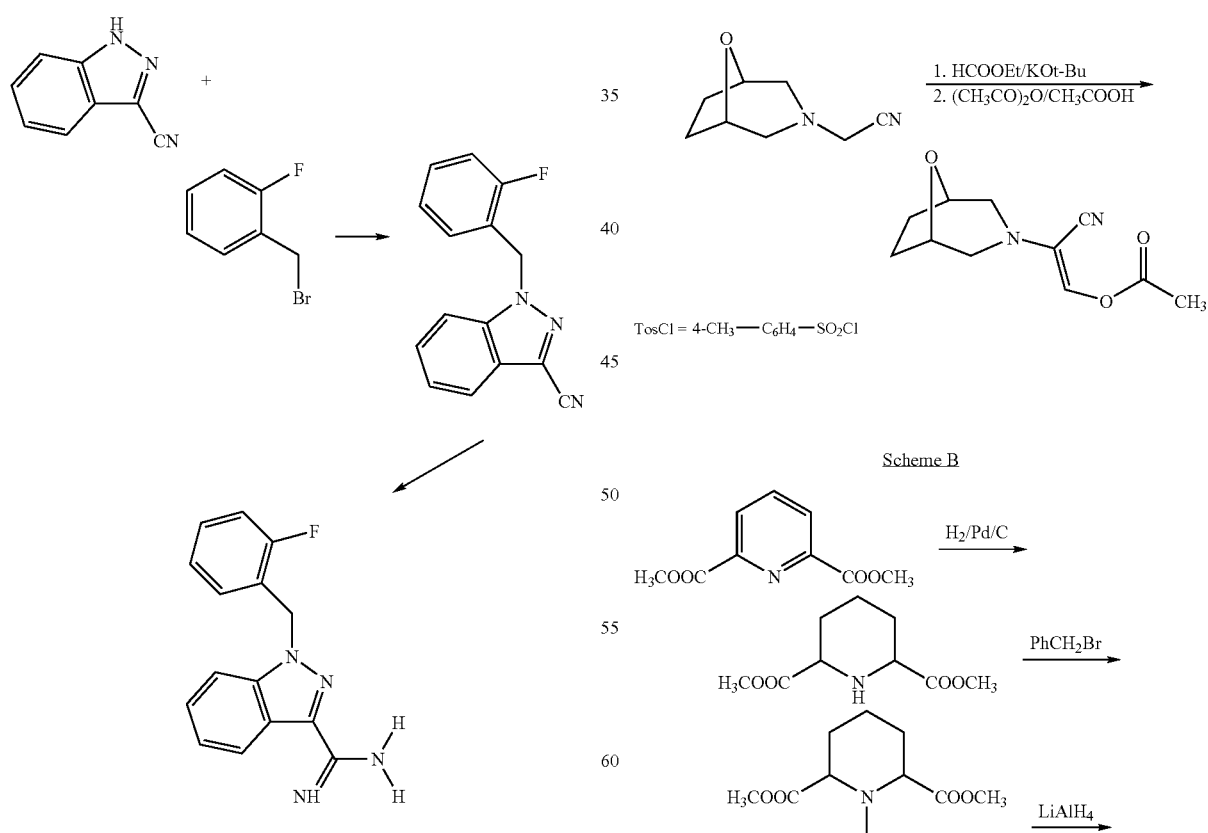

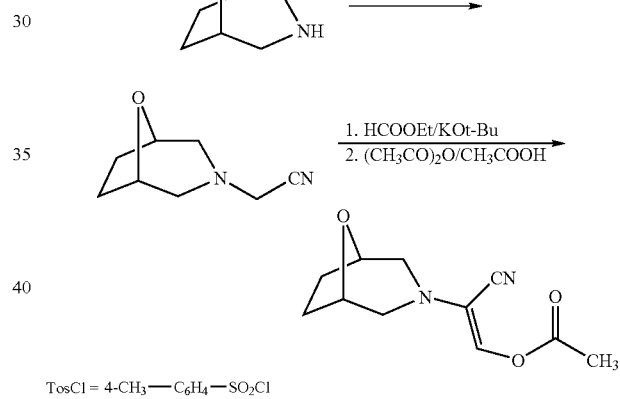

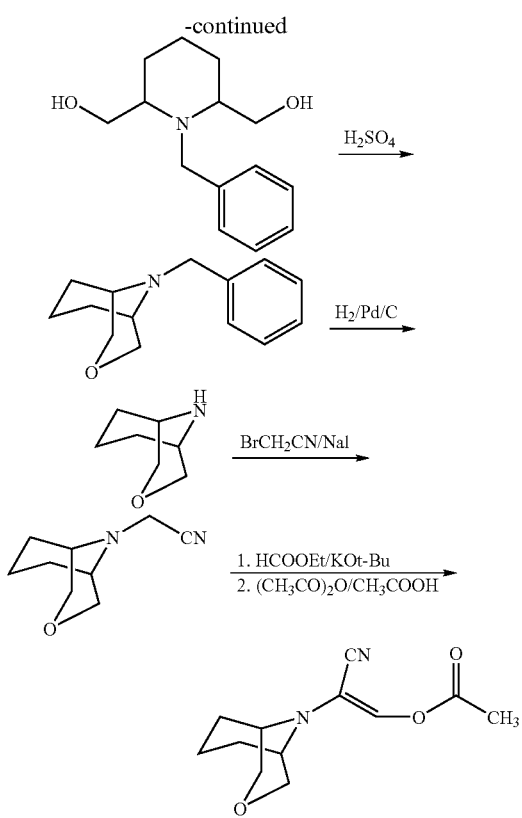

The corresponding starting compounds 2,5-bis(hydroxymethyl)tetrahydrofuran and dimethyl pyridine-2,6-dicarboxylate can be purchased (e.g. from Aldrich) or can be obtained in a conventional manner by routes known to the skilled worker.

In the case of the bicyclic [3.2.1]octane the bicyclic system is assembled for example by reacting the bishydroxymethyltetrahydrofuran derivative (activated as bistosylate) with benzylamine by a nucleophilic substitution reaction under conditions conventionally used for such reactions. It is preferred according to the invention to carry out the reaction in an organic solvent, for example a hydrocarbon, preferably an aromatic hydrocarbon and especially toluene, using a 2-5-fold excess of the amine, preferably under atmospheric pressure with stirring of the reaction solution for a plurality of hours, for example 2 hours, at elevated temperature, for example 60-130° C., preferably 80-120° C., in particular 100° C.

In the case of the bicyclic [3.3.1]nonane, the bicyclic system is assembled for example by an intramolecular nucleophilic substitution reaction of the two hydroxy groups of the piperidine-2,6-dihydroxymethyl derivative under conditions conventionally used for such reactions. It is preferred according to the invention to carry out the reaction under acidic conditions, for example in the presence of concentrated sulfuric acid, preferably under atmospheric pressure and with stirring of the reaction solution for a plurality of hours, for example 24 hours, at elevated temperature, for example 60-200° C., preferably 80-190° C., in particular 175° C. The piperidine-2,6-dihydroxymethyl derivative required for this can be prepared from pyridine-2,6-dicarboxylic acid methyl ester by hydrogenation under the conditions conventionally used for such reactions, for example with hydrogen over a palladium/activated carbon catalyst, to give the corresponding piperidine-2,6-dicarboxylic acid methyl ester, benzylation of the ring nitrogen with, for example, benzyl bromide (cf. Goldspink, Nicholas J.; Simpkins, Nigel S.; Beckmann, Marion; Syn.Lett.; 8; 1999; 1292-1294) and subsequent reduction of the carboxylic ester groups to the corresponding hydroxymethyl radicals under conditions conventionally used for such reactions, for example with lithium aluminum hydride in an organic solvent, for example an ether, preferably diethyl ether, using a 2-5-fold of the reducing agent, preferably under atmospheric pressure with stirring of the reaction solution for a plurality of hours, for example 3 hours, at elevated temperature, for example 30-100° C., preferably 30-70° C., in particular under reflux of the solvent used.

The bicyclic system obtained in this way can in each case be converted by elimination of the benzylic protective group under the conditions conventionally used for such reactions, for example with hydrogen over a palladium/activated carbon catalyst in an organic solvent, for example an alcohol, preferably ethanol, preferably under elevated pressure of 50-200 bar, preferably 100 bar, with stirring of the reaction solution for a plurality of hours, for example 5 hours, at elevated temperature, for example 60-130° C., preferably 80-120° C., in particular 100° C., into the corresponding bicyclic amines. These can be converted by reaction with suitable acetonitrile derivatives, for example with haloacetonitriles and preferably with bromoacetonitrile, under conditions conventionally used for such reactions, for example in an organic solvent such as N,N-dimethylformamide (DMF), using a slight excess of the acetonitrile derivative in the presence of a base, for example an amine such as N,N-diisopropylethylamine, and a halide such as sodium iodide, preferably under atmospheric pressure with stirring of the reaction solution for a plurality of hours, for example 24 hours, at elevated temperature, for example 40-130° C., preferably 40-100° C., in particular 60° C., into the corresponding N-methylnitrile derivatives. The compounds of the formula (III) can be prepared therefrom finally by reaction with a formic ester such as, for example, ethyl formate under conditions conventionally used for such reactions, for example in an organic solvent, for example an ether, preferably a cyclic ether such as tetrahydrofuran (THF), using a 2-5-fold excess of formic ester, preferably under atmospheric pressure with stirring of the reaction solution for a plurality of minutes, for example 20-60 minutes, at room temperature, and subsequent acetylation with acetic anhydride in the presence of acetic acid under conditions conventionally used for such reactions, for example using a slight excess of acetic anhydride, preferably under atmospheric pressure with stirring of the reaction solution for a plurality of minutes, for example 20-60 minutes.

Reaction of the compounds of the formulae (II) and (III) to give the compounds of the formula (I) can be carried out by employing the reactants in equimolar amounts or using the compound of the formula (III) in slight excess in an organic solvent, for example a hydrocarbon, preferably an aromatic hydrocarbon and in particular toluene, preferably under atmospheric pressure with stirring of the reaction solution for a plurality of hours, for example 12 hours, at elevated temperature, for example 80-160° C., preferably 100-150° C., in particular 120° C.

The compounds of the formula (IV) are commercially available (e.g. from Mercachem) or can be prepared in a manner known to the skilled worker.

Reaction of the compounds of the formulae (II) and (IV) to give the compounds of the formula (VI) can be carried out by employing the reactants in equimolar amounts or using the compounds of the formula (IV) in slight excess in an organic solvent, for example a hydrocarbon, preferably an aromatic hydrocarbon and in particular toluene, preferably under atmospheric pressure with stirring of the reaction solution for a plurality of hours, for example 12 hours, at elevated temperature, for example 80-160° C., preferably 100-150° C., in particular 140° C.

Conversion of the compounds of the formula (V) into compounds of the formula (VI) can be carried out by reacting the compounds of the formula (V) with a halogenating agent, where appropriate in an organic solvent conventionally used for such reactions, such as, for example, dimethylformamide (DMF), preferably under atmospheric pressure with stirring of the reaction solution for a plurality of hours, for example 3 hours, at elevated temperature, for example 80-160° C., preferably 100-120° C. The halogenating agent which can preferably be employed according to the invention is $POCl_3$.

Conversion of compounds of the formula (VI) into compounds of the invention of the formula (I) can be carried out by reacting the compounds of the formula (VI) with aqueous ammonia solution, preferably under elevated pressure, for example by the reaction proceeding in an autoclave so that the reaction takes place under the autogenous pressure of the reaction mixture, with stirring of the reaction solution for a plurality of hours, for example 12 hours, at elevated temperature, for example 80-160° C., preferably 100-150° C., in particular 140° C.

The compounds of the invention show a valuable range of pharmacological effects which could not have been predicted.

The compounds of the invention increase the cGMP levels in neurons and thus represent active ingredients for controlling central nervous system diseases characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff's psychosis.

The compounds of the invention also lead to vasorelaxation, platelet aggregation inhibition and to a reduction in blood pressure, and to an increase in the coronary blood flow. These effects are mediated by direct stimulation of soluble guanylate cyclase and an intracellular cGMP increase. In addition, the compounds of the invention may enhance the effect of substances which increase the cGMP level, such as, for example, EDRF (endothelium derived relaxing factor), NO donors, protoporphyrin IX, arachidonic acid or phenylhydrazine derivatives.

They can therefore be employed in medicaments for the treatment of cardiovascular disorders such as, for example, for the treatment of high blood pressure and heart failure, stable and unstable angina pectoris, peripheral and cardiac vascular disorders, of arrhythmias, for the treatment of thromboembolic disorders and ischemias such as myocardial infarction, stroke, transistorily and ischemic attacks, disturbances of peripheral blood flow, prevention of restenoses as after thrombolysis therapies by use in stents for example, percutaneously transluminal angioplasties (PTAs), percutaneously transluminal coronary angioplasties (PTCAs), bypass operations and for the treatment of arteriosclerosis, asthmatic disorders, osteoporosis, gastroparesis, glaucoma and diseases of the urogenital system such as, for example, incontinence, prostate hypertrophy, erectile dysfunction and female sexual dysfunction.

They are also suitable for the treatment of central nervous system disorders such as states of anxiety, tension and depression, CNS-related sexual dysfunctions and sleep disturbances, and for controlling pathological disturbances of the intake of food, stimulants and addictive substances.

The compounds of the invention are additionally suitable for controlling cerebral blood flow and may represent effective agents for controlling migraine.

They are also suitable for the prophylaxis and control of the sequelae of cerebral infarctions such as stroke, cerebral ischemias and craniocerebral trauma. The compounds of the invention can likewise be employed for controlling states of pain.

In addition, the compounds of the invention have an anti-inflammatory effect.

Furthermore, the invention encompasses the combination of the compounds of the invention with organic nitrates and NO donors.

Organic nitrates and NO donors for the purposes of the invention are generally substances which release NO or NO precursors. Preference is given to sodium nitroprusside, nitroglycerine, isosorbide dinitrate, isosorbide mononitrate, molsidomine and SIN-1.

In addition, the invention encompasses the combination with compounds which inhibit breakdown of cyclic guanosine monophosphate (cGMP). These are in particular inhibitors of phosphodiesterases 1, 2 and 5; nomenclature of Beavo and Reifsnyder (1990), TiPS 11 pp. 150 to 155. These inhibitors potentiate the effect of the compounds of the invention, and the desired pharmacological effect is increased.

The in vitro effect of the compounds of the invention can be shown in the following assays:

Increase of cGMP in Primary Cortical Neurons

Rat embryos (embryonic day 17-19) are decapitated, and the cerebrum is removed and incubated with 5 ml of papain solution and 250 µl of DNAse (papain kit from Cell-System) at 37° C. for 30 min, homogenized using a Pasteur pipette and centrifuged at 1200 rpm for 5 min. The supernatant is removed, the cell pellet resuspended (in 2.7 ml of EBSS [Earl's balanced salt solution], 300 µl of ovomucoid/albumin (conc.) solution, 150 µl of DNAse; papain kit from Cell-System), layered over 5 ml of ovomucoid/albumin solution and centrifuged at 700 rpm for 6 min. The supernatant is removed, the cells are resuspended in cultivation medium (Gibco neurobasal medium, B27 Supplement 50×1 ml/100 ml, 2 mM L-glutamine), counted (approx. 150 000 cells/well) and plated out on poly-D-lysine-coated 96-well plates (Costar) with 200 µl/well. After 6-7 days at 37° C. (5% $CO_2$), the neurons are freed of culture medium and washed once with assay buffer (154 mM NaCl, 5.6 mM KCl, 2.3 mM $CaCl_2 2H_2O$, 1 mM $MgCl_2$, 5.6 mM glucose, 8.6 mM HEPES (4-(2-hydroxyethyl)piperazine-1-ethanesulfonic acid), pH=7.4). 100 µl/well test substance are dissolved in assay buffer and then 100 µl/well IBMX (3-isobutyl-1-methylxanthine; dissolved in 50 mM ethanol, diluted with assay buffer to a final concentration of 100 µM) are added. After incubation at 37° C. for 20 min, the assay buffer is replaced by 200 µl/well of lysis buffer (cGMP EIA RPN 226 from Amersham Pharmacia Biotech), and the cGMP content of the lystates is determined using an EIA assay kit.

A concentration of 0.1 μM of Example 1 leads to a statistically significant increase in cGMP.

Vasorelaxant Effect in Vitro

Rabbits are stunned by a blow to the back of the neck and are exsanguinated. The aorta is removed, freed of adherent tissue, divided into rings 1.5 mm wide and put singly under tension in 5 ml organ baths containing carbogen-gassed Krebs-Henseleit solution at 37° C. with the following composition (mM): NaCl: 119; KCl: 4.8; $CaCl_2 \times 2$ $H_2O$: 1; $MgSO_4 \times 7$ $H_2O$: 1.4; $KH_2PO_4$: 1.2; $NaHCO_3$: 25; glucose: 10. The force of contraction is detected with Statham UC2 cells, amplified and digitized via A/D converters (DAS-1802 HC, Keithley Inistruments Munich) and recorded in parallel on chart recorders. A contraction is generated by adding phenylephrine to the bath cumulatively in increasing concentration. After several control cycles, the substance to be investigated (dissolved in 5 μl of DMSO) is investigated in each further run in increasing dosage in each case, and the height of the contraction is compared with the height of the contraction reached in the last control cycle (control value). The concentration necessary to reduce the height of the control value by 50% ($IC_{50}$) is calculated from this.

Determination of the Liver Clearance In Vitro

Rats are anesthetized, heparinized, and the liver is perflised in situ via the portal vein. Primary rat hepatocytes are then obtained ex vivo from the liver using collagenase solution. $2.10^6$ hepatocytes per ml were incubated at 37° C. with the same concentration in each case of the compound to be investigated. The decrease of the substrate to be investigated over time was determined bioanalytically (HPLC/UV, HPLC/fluorescence or LC/MSMS) at 5 points in time in each case in the period from 0-15 min after the start of incubation. From this, the clearance was calculated by means of the cell count and liver weight.

Determination of the Plasma Clearance In Vivo

The substance to be investigated is administered as a solution intravenously to rats via the tail vein. At fixed points in time, blood is taken from the rats, heparinized and plasma is obtained therefrom by conventional measures. The substance is quantified bioanalytically in the plasma. The pharmacokinetic parameters are calculated from the plasma concentration-time courses determined in this way by means of conventional non-compartmental methods used for this purpose.

The suitability of the compounds of the invention for the treatment of disorders of perception, concentration, learning and/or memory can be shown for example in the following animal model:

Determination of the Learning and Memory in the Social Recognition Test

Adult Wistar rats (Winkelmann, Borchen; 4-5 months) and 4-5-week old pups are accustomed to their new environment for one week, with 3 animals being housed in each cage (Makrolon type IV) in a 12 h day-night rhythm (light on at 06:00) with water and food ad libitum. Usually, 4 groups of 10 animals (1 vehicle control group, 3 substance-treated groups) are tested. Firstly, all animals undergo a habituation run as in trial 1 but without substance or vehicle administration. The test substances are administered directly after trial 1. The social memory is measured in trial 2 after 24 h.

Trial 1: 30 min before testing, the adult rats are housed singly in cages (Makrolon type IV). 4 min before testing, a box consisting of two aluminum side walls, an aluminum back wall and a Plexiglas front (63×41×40 cm) is fitted over the cage, and the lid of the cage is removed. A pup is put with the adult rats in the cage, and the social interaction (e.g. sniffing) is timed for 2 min with a stopclock. The animals are then returned to their cage.

Trial 2: The test is repeated with the same animals after 24 h in analogy to trial 1. The difference between the social interaction time in trial 1 and trial 2 is taken as a measure of the social memory.

The compounds of the invention are suitable for use as medicaments for humans and animals.

The present invention includes pharmaceutical preparations which, besides inert, nontoxic, pharmaceutically suitable excipients and carriers, comprise one or more compounds of the invention, or which consist of one or more compounds of the invention, and processes for producing these preparations.

The compounds of the invention are to be present in these preparations in a concentration of from 0.1 to 99.5% by weight, preferably from 0.5 to 95% by weight, of the complete mixture.

The pharmaceutical preparations may, apart from the compounds of the invention, also comprise other active pharmaceutical ingredients.

The pharmaceutical preparations mentioned above can be produced in a conventional way by known methods, for example with the excipient(s) or carrier(s).

The novel active ingredients can be converted in a known manner into the usual formulations such as tablets, coated tablets, pills, granules, aerosols, syrups, emulsions, suspensions and solutions, using inert, nontoxic, pharmaceutically suitable carriers or solvent. In these cases, the therapeutically effective compound is to be present in each case in a concentration of about 0.5 to 90% by weight of the complete mixture, i.e. in amounts which are sufficient to achieve the indicated dosage range.

The formulations can be produced for example by diluting the active ingredients with solvents and/or carriers, where appropriate using emulsifiers and/or dispersants, it being possible for example in the case where water is used as diluent where appropriate to use organic solvents as auxiliary solvents.

Administration can take place in a conventional way, preferably orally, transdermally or parenterally, in particular perlingually or intravenously. However, it can also take place by inhalation through the mouth or nose, for example with the aid of a spray, or topically via the skin.

It has generally proved to be advantageous to administer amounts of about 0.001 to 10 mg/kg, on oral administration preferably about 0.005 to 3 mg/kg, of body weight to achieve effective results.

It may nevertheless be necessary where appropriate to deviate from the stated amounts, in particular as a function of the body weight or the nature of the administration route, the individual response to the medicament, the nature of its formulation and the time or interval over which administration takes place. Thus, it may be sufficient in some cases to make do with less than the aforementioned minimum amount, where in other cases the stated upper limit must be exceeded. If larger amounts are administered, it may be advisable to divide these into a plurality of single doses over the day.

Abbreviations:
CI chemical ionization (in MS)
dist. distilled
DMSO dimethyl sulfoxide
EI electron impact ionization (in MS)
ESI electrospray ionization (in MS)
GC gas chromatography HPLC high pressure, high performance liquid chromatography
LC-MS coupled liquid chromatography-mass spectroscopy
MS mass spectroscopy
NMR nuclear magnetic resonance spectroscopy
$R_f$ retention index (in TLC)
$R_t$ retention time (in HPLC)
TLC thin-layer chromatography Analytical Methods:
GC-MS
carrier gas: Helium
Flow rate: 1.5 ml/min
Starting temperature: 60° C.
Temperature gradient: 14° C./min up to 300° C., then 1 min constant at 300° C.
column: HP-5 30 m×320 μm×0.25 μm (film thickness)
Starting time: 2 min
Front injector temp.: 250° C.
LC-MS
Instrument: Finnigan MAT 900S, TSP: P4000, AS3000, UV3000HR
Column: Symmetry C 18,150 mm×2.1 mm, 5.0 μm
Eluent A: Acetonitrile
Eluent B: water+0.6 g of 30% strength hydrochloric acid/L
Gradient: 0.0 min 10% A→4.0 min 90% A→9 min 90% A
Oven: 50° C.
Flow rate 0.6 ml/min
UV detection: 210 nm.

Starting Compounds:

EXAMPLE I (E/Z)-2-Cyano-2-(8-oxa-3-azabicyclo[3.2.1]oct-3-yl)ethenyl acetate

Stage Ia 2,5-Anhydro-3,4-dideoxy-1,6-bis-O-[(4-methylphenyl)sulfonyl]hexitol

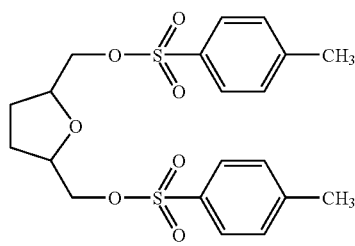

34.0 g (261 mmol) of 2,5-bis(hydroxymethyl)tetrahydrofuran are dissolved in 260 ml of dichloromethane. A solution of 99.0 g (521 mmol) of p-toluenesulfonyl chloride in 52 ml of pyridine and 130 ml of dichloromethane is added dropwise thereto. After stirring at room temperature for 24 hours, the precipitate is filtered off with suction and washed with dichloromethane. The filtrate and the washing phases are combined, washed with dilute hydrochloric acid and then with saturated aqueous sodium bicarbonate solution, dried over magnesium sulfate and evaporated to dryness. The crude product is recrystallized from ethanol. 112 g (98% of theory) of product are obtained.
Melting point: 125° C.
MS (CIpos): m/z =441 (M+H)+.

Stage Ib)

3-Benzyl-8-oxa-3-azabicyclo[3.2.1]octane

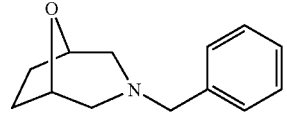

112 g (250 mmol) of.2,5-anhydro-3,4-dideoxy-1,6-bis-O-[(4-methylphenyl)sulfonyl]-hexitol from Example Ia) and 90.7 g (840 mmol) of benzylamine in 500 ml of toluene are heated under reflux for 20 hours. The precipitate is then filtered-off with suction and washed with toluene. The combined toluene phases are concentrated in a rotary evaporator and distilled in vacuo. After a benzylamine fore-run, 28.2 g (54% of theory) of product are obtained.
Boiling point: 96-99° C./8 mbar
MS (CIpos): m/z=204 (M+H)+.

Stage IC)

8-Oxa-3-azabicyclo[3.2.1]octane hydrochloride

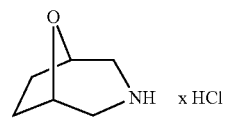

28.2 g (136 mmol) of 3-benzyl-8-oxa-3-azabicyclo[3.2.1]octane from Example Ib) are dissolved in 200 ml of ethanol, 5.00 g of palladium on activated carbon (10%) are added, and hydrogenation is carried out with 100 bar of hydrogen in an autoclave at 100° C. The catalyst is filtered off with suction and the filtrate is mixed with 11.9 ml of concentrated hydrochloric acid and concentrated in a rotary evaporator. Acetone is added to the residue, and the resulting precipitate is filtered off with suction and dried over phosphorus pentoxide. 17.0 g (84% of theory) of product are obtained.
Melting point: 209-221° C.
MS (CIpos): m/z=114 (M+H)+.

Stage Id)

8-Oxa-3-azabicyclo[3.2.1]oct-3-ylacetonitrile

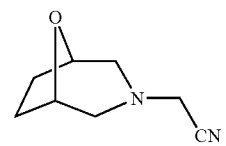

1.54 g (10.3 mmol) of 8-oxa-3-azabicyclo[3.2.1]octane hydrochloride from Example Ic) are introduced into 20 ml of N,N-dimethylformamide and, while cooling in ice, 2.94 g (22.7 mmol) of N,N-diisopropylethylamine are added. After stirring at room temperature for 30 minutes, 1.36 g (11.4 mmol) of bromoacetonitrile are added dropwise, 89.9 mg (0.60 mmol) of sodium iodide are added, and the mixture is stirred at 60° C. overnight. The reaction mixture is then evaporated to dryness and the residue is dissolved in a little dichloromethane. The solution is filtered through silica gel with dichloromethane/methanol 50:1 as eluent, and the resulting product fractions are dried under high vacuum. 1.24 g (69% of theory) of the product are obtained.
$R_f$=0.80 (dichloromethane/methanol 20:1)
GC-MS: $R_t$=11.23 min.
MS (CIpos.): m/z=153 (M+H)$^+$.
Stage Ie)

(E/Z)-2-Cyano-2-(8-oxa-3-azabicyclo[3.2.1]oct-3-yl)ethenal acetate

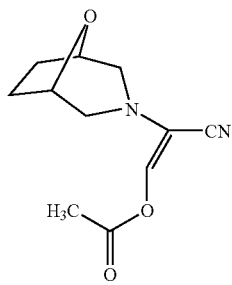

2.00 g (17.8 mmol) of potassium tert-butoxide are introduced into 10 ml of anhydrous tetrahydrofuran. While cooling in ice, a solution of 1.23 g (8.08 mmol) of 8-oxa-3-azabicyclo[3.2.1]oct-3-ylacetonitrile from Example Id) and 1.37 g (17.8 mmol) of ethyl formate in 5 ml of tetrahydrofuran are added dropwise. After stirring at room temperature for 1 hour, a solution of 1.16 g (11.3 mmol) of acetic anhydride and 1.07 g (17.8 mmol) of acetic acid is added dropwise while cooling in ice, and the mixture is stirred at room temperature for 1 hour. The mixture is subsequently filtered-through silica gel with dichloromethane as eluent. The product fractions are evaporated to dryness at 40° C. 2.03 g (54% of theory) of the product are obtained and are employed without further purification in the next reaction.
$R_f$=0.64 (dichloromethane/methanol 20:1).

EXAMPLE II (E)-2-Cyano-2-(3-oxa-9-azabicyclo[3.3.1]non-9-yl) ethenyl acetate

Staze IIa)

[1-Benzyl-6-(hydroxymethyl)-2-piperidinyl]methanol

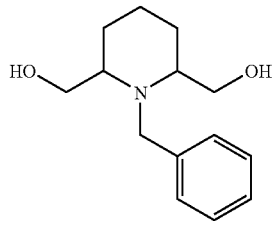

19.0 g (500 mmol) of lithium aluminum hydride are introduced into 300 ml of anhydrous diethyl ether, and a solution of 75.0 g (250 mmol) of dimethyl 1-benzyl-2,6-piperidinedicarboxylate [from dimethyl pyridine-2,6-dicarboxylate by hydrogenation with hydrogen over palladium on activated carbon and subsequent reaction of the dimethyl 2,6-piperidinedicarboxylate formed with benzyl bromide, according to: Goldspink, Nicholas J., Simpkins, Nigel S., Beckmann, Marion, Syn. Lett. 8, 1292-1294 (1999)] in 300 ml of anhydrous diethyl ether is added dropwise thereto. The mixture is then heated under reflux for 3 h, cautiously hydrolyzed with 40 ml of water and mixed with 20 ml of 15% strength aqueous potassium hydroxide solution. The precipitate is filtered off with suction and boiled with dioxane. The combined filtrates are dried over magnesium sulfate and evaporated to dryness in a rotary evaporator. The crude product is subjected to a vacuum distillation. 53.3 g (91% of theory) of product are obtained.
Boiling point: 170° C./0.2 mbar.
Stage IIb)

9-Benzyl-3-oxa-9-azabicyclo[3.3.1]nonane

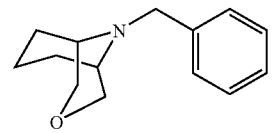

40 g (170 mmol) of [1-benzyl-6-(hydroxymethyl)-2-piperidinyl]methanol from Example IIa) are stirred in 129 ml of 66% strength sulfuric acid at 175° C. overnight. Cooling to room temperature is followed by neutralization with sodium carbonate, rendering alkaline with sodium hydroxide and extraction several times with dichloromethane. The combined organic phases are dried over magnesium sulfate and evaporated to dryness in a rotary evaporator. The residue is distilled in vacuo. 26.5 g (72% of theory) of the product are obtained.
Boiling point: 101-103° C./8 mbar.
MS (CIpos.): m/z=218 (M+H)$^+$.
Stage IIc)

3-Oxa-9-azabicyclo[3.3.1]nonane hydrochloride

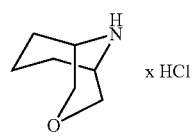

26.0 g (120 mmol) of 9-benzyl-3-oxa-9-azabicyclo[3.3.1] nonane from Example IIb) are dissolved in 200 ml of ethanol, 5.00 g of palladium on activated carbon (10%) are added, and hydrogenation is carried out with 100 bar of hydrogen in an autoclave at 100° C. The catalyst is filtered off with suction and the filtrate is mixed with 10.9 ml of concentrated hydrochloric acid and concentrated in a rotary evaporator. The residue is mixed with acetone, and the resulting precipitate is filtered off with suction and dried over phosphorus pentoxide. 12.0 g (81% of theory) of the product are obtained.
$^1$H-NMR (400 MHz, D$_2$O): δ=1.68-1.76 (m, 1H), 2.08-2.15 (m, 4H), 2.32-2.45 (m, 1H), 3.56 (m$_c$, 2H), 4.07-4.17(m, 4H) ppm.
Stage IId)

3-Oxa-9-azabicyclo[3.3.1]non-9-ylacetonitrile

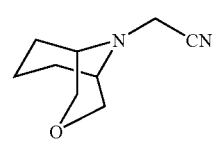

2.00 g (12.2 mmol) of 3-oxa-9-azabicyclo[3.3.1]nonane hydrochloride from Example IIc) are introduced into 20 ml of N,N-dimethylformamide and, while cooling in ice, 3.10 g (26.9 mmol) of N,N-diisopropylethylamine are added. After stirring at room temperature for 30 minutes, 1.61 g (13.4 mmol) of bromoacetonitrile are added dropwise, 60.0 mg (0.40 mmol) of sodium iodide are added, and the mixture is stirred at 60° C. overnight. The reaction mixture is then evaporated to dryness and the residue is dissolved in a little dichloromethane. The solution is filtered through silica gel with dichloromethane/methanol 50:1 as eluent, and the resulting product fractions are dried under high vacuum. 1.59 g (76% of theory) of the product are obtained.

$R_f$=0.79 (dichloromethane/methanol 20:1)
GC-MS: $R_t$=12.55 min.
MS (CIpos.): m/z=167 (M+H)⁺.

Stage IIe)

(E)-2-Cyano-2-(3-oxa-9-azabicyclo[3.3.1]non-9-yl)ethenyl acetate

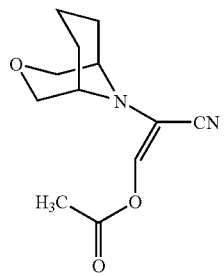

2.35 g (20.9 mmol) of potassium tert-butoxide are introduced into 10 ml of anhydrous tetrahydrofuran. While cooling in ice, a solution of 1.55 g (9.50 mmol) of 3-oxa-9-azabicyclo [3.3.1]non-9-ylacetonitrile from Example IId) and 1.55 g (20.9 mmol) of ethyl formate in 5 ml of tetrahydrofuran is added dropwise. After stirring at room temperature for 1 hour, a solution of 1.36 g (13.3 mmol) of acetic anhydride and 1.26 g (20.9 mmol) of acetic acid is added dropwise while cooling in ice, and the mixture is stirred at room temperature for 1 hour. The mixture is subsequently filtered through silica gel with dichloromethane as eluent. The product fractions are evaporated to dryness at 40° C. 1.59 g (39% of theory) of the product are obtained and are employed without further purification in the next reaction.

$R_f$=0.66 (dichloromethane/methanol 20:1).

EXAMPLE III 1-(2-Fluorobenzyl)-1H-indazole-3-carboximidamide

Stake IIIa)

1-(2-Fluorobenzyl)-3-cyanoindazole

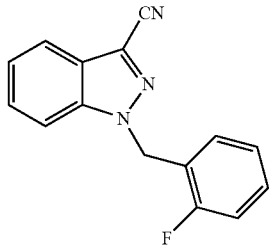

12.00 g (83.9 mmol) of 3-cyanoindazole are dissolved under argon in 100 ml of absolute tetrahydrofuran, and 20.60 g (109.0 mmol) of 2-fluorobenzyl bromide are added. While cooling in ice, 2.55 g (100.0 mmol) of sodium hydride (95%) are added in portions. The reaction mixture is stirred at room temperature overnight, and the solvent is reduced in vacuo to one quarter of the original volume. The mixture is diluted with dist. water and extracted with ethyl acetate. The combined organic phases are dried over magnesium sulfate and filtered, and the solvent is removed in vacuo. 19.50 g (93% of theory) of the product are obtained.

$R_f$=0.69 (cyclohexane/ethyl acetate 1:1).

Stage IIIb)

1-(2-Fluorobenzyl)indazole-3-amidinium chloride

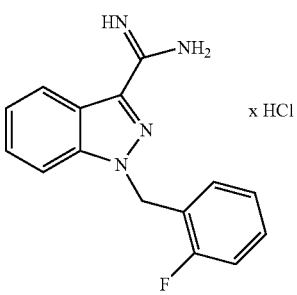

A solution of 20.0 g (79.9 mmol) of 1-(2-fluorobenzyl)-3-cyanoindazole in 200 ml of absolute methanol is added to a sodium methanolate solution freshly prepared from 190 mg (8.26 mmol) of sodium in 30 ml of absolute methanol, and the mixture is stirred at 40° C. for 22 h. After addition of 0.46 ml of acetic acid and 4.30 g (80.4 mmol) of ammonium chloride, the mixture is evaporated to dryness. The residue is suspended in acetone, and the remaining precipitate is filtered off and dried. 20.5 g (84% of theory) of product are obtained.

Melting point: >230° C.

MS (EI): m/z (%)=268 (31, M⁺ of the free base), 251 (15), 109 (100).

Stage IIIc)

1-(2-Fluorobenzyl)-1H-indazole-3-carboximidamide

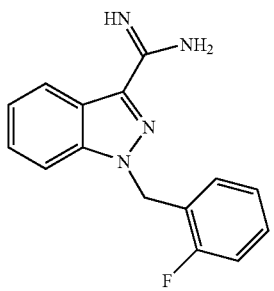

2.61 g (24.61 mmol) of sodium carbonate as 10% strength aqueous solution are added to a suspension of 5.00 g (16.41 mmol) of 1-(2-fluorobenzyl)indazole-3-amidinium chloride from Example IIIb) in 100 ml of ethyl acetate, and the mixture is stirred at room temperature for 90 minutes. One molar sodium hydroxide solution is added until the phases have separated. The organic phase is washed with saturated sodium chloride solution, dried over magnesium sulfate and filtered, and the solvent is removed in vacuo. 3.33 g (76% of theory) of the product are obtained.

MS (ESIpos): m/z=269 (M+H)⁺

¹H-NMR (300 MHz, DMSO-d₆): δ=5.82 (s, 2H), 6.67 (br. s, 2H), 7.10-7.33 (m, 5H), 7.38-7.57 (m, 2H), 7.78 (d, 1H), 8.38 (d, 1H) ppm.

Exemplary Embodiments:

EXAMPLE 1

2-[1-(2-Fluorobenzyl)-1H-indazol-3-yl]-5-(3-oxa-9-azabicyclo[3.3.1]non-9-yl)-4pyrimidinylamine

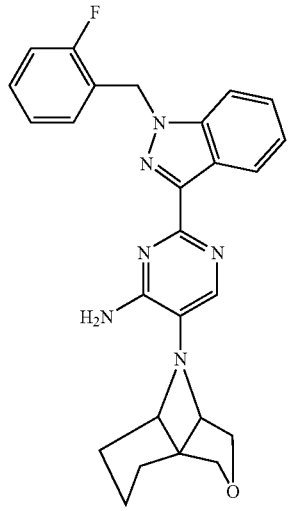

500 mg (1.86 mmol) of 1-(2-fluorobenzyl)-1H-indazol-3-carboximidamide (Example III) and 594 mg (2.52 mmol) of freshly prepared (E)-2-cyano-2-(3-oxa-9-azabicyclo-[3.3.1]non-9-yl)ethenyl acetate (Example II) are suspended in 10 ml of toluene and stirred at 120° C. overnight. The solvent is removed in vacuo, and the residue is purified by preparative HPLC. The resulting crude product is stirred in ethyl acetate/diethyl ether. The solid is filtered off and dried. 37 mg (4% of theory) of the product are obtained.

LC-MS: $R_t$=2.05 min.
MS (ESIpos): m/z=455 (M+H)$^+$
$R_f$=0.37 (dichloromethane/methanol 20:1)
$^1$H-NMR (200 MHz, DMSO-d$_6$): δ=1.60-1.83 (m, 3H), 1.97-2.22 (m, 2H), 2.35-2.65 (m, 1H), 3.78 (d, 2H), 4.04 (d, 2H), 5.77 (s, 2H), 6.34 (s, 2H), 7.02-7.51 (m, 6H), 7.73 (d, 1H), 8.18 (s, 1H), 8.63 (d, 1H) ppm.

EXAMPLE 2

2-[1-(2-Fluorobenzyl)-1H-indazol-3-yl]-5-(8-oxa-3-azabicyclo[3.2.1]oct-3-yl)-4-pyrimidinylamine

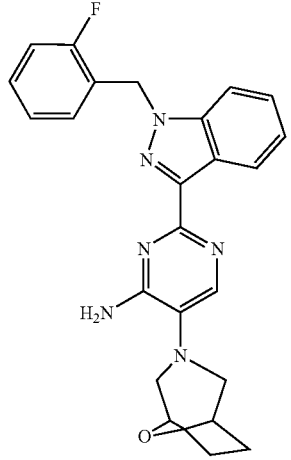

The compound is prepared in analogy to the method for Example 1 using the appropriate starting materials 1-(2-fluorobenzyl)-1H-indazole-3-carboximidamide (Example III) and (E/Z)-2-cyano-2-(8-oxa-3-azabicyclo[3.2.1]oct-3-yl)ethenyl acetate (Example I). The yield of product is 166 mg (21% of theory).

LC-MS: $R_t$=1.94 min.
MS (ESIpos): m/z=431 (M+H)$^+$
$R_f$=0.22 (dichloromethane/methanol 20:1)
$^1$H-NMR (200 MHz, DMSO-d$_6$): δ=1.78-1.95 (m, 2H), 2.13-2.28 (m, 2H), 2.93 (s, 4H), 4.38 (br. s, 2H), 5.93 (s, 2H), 7.10-7.45 (m, 5H), 7.58 (t, 1H), 7.82 (s, 1H), 7.99(d, 1H), 8.69 (d, 1 H) ppm.

The invention claimed is:
1. A compound of the formula

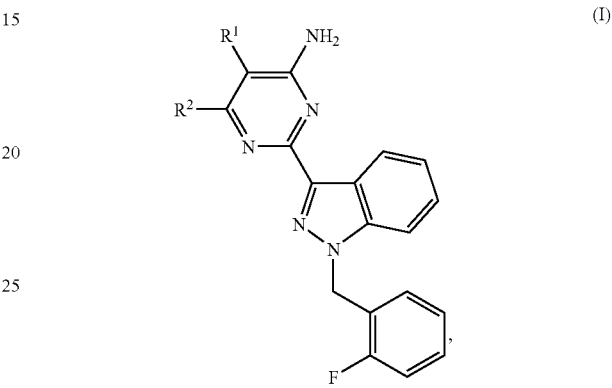

(I)

in which
R$^1$ is

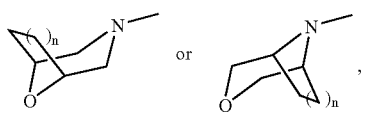

where
n is 1 or 2, and
R$^2$ is hydrogen or NH$_2$,
or a salt, solvate, or solvate of a salt thereof.
2. A compound as claimed in claim 1,
where
R$^1$ is

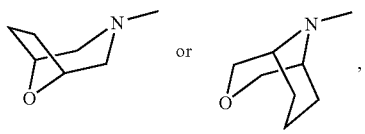

and
R$^2$ is hydrogen or NH$_2$
or a salt, solvate, or solvate of a salt thereof.
3. A compound as claimed in claim 1,
in which
R$^1$ is

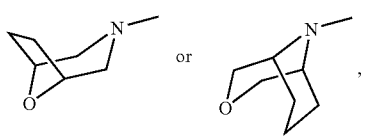

and
R$^2$ is hydrogen,
or a salt, solvate, or solvate of a salt thereof.

4. A process for preparing a compound of the formula (I) by reacting a compound of the formula

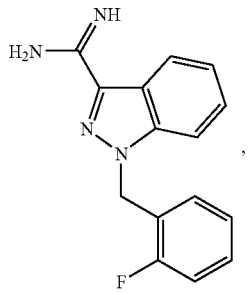
(II)

A) with a compound of the formula

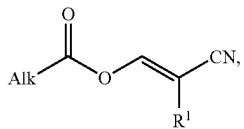
(III)

where $R^1$ has the meanings indicated in claim 1 and Alk is $C_1$-$C_4$-alkyl, or B) with a compound of the formula

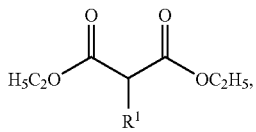
(IV)

where $R^1$ has the meanings indicated in claim 1, to give a compound of the formula

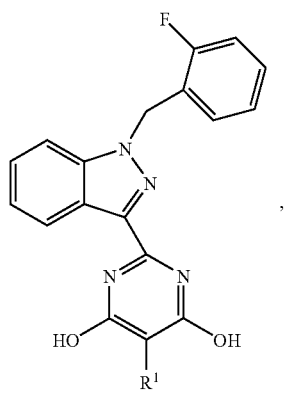
(V)

where $R^1$ has the meanings indicated in claim 1, and subsequently reacting with a halogenating agent to give a compound of the formula

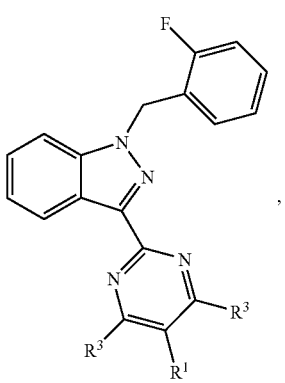
(VI)

where $R^1$ has the meanings indicated in claim 1, and
$R^3$ is halogen, and final reaction with aqueous ammonia solution with heating under elevated pressure, and by reacting the resulting compound of the formula (I) where appropriate with an appropriate (i) solvent and/or (ii) base or acid to give a salt, solvate, or solvate of a salt thereof.

5. A pharmaceutical compositon comprising at least one of the compounds as claimed in claim 1, mixed together with at least one pharmaceutical acceptable, essentially nontoxic carrier or excipient.

\* \* \* \* \*